United States Patent [19]
Dupuy et al.

[11] Patent Number: 6,086,893
[45] Date of Patent: Jul. 11, 2000

[54] HELICOBACTER LACTOFERRIN RECEPTOR

[75] Inventors: Monique Dupuy, St Genis les Ollieres; Ling Lissolo, Marcy l'Etoile; Marie-José Bernadette Quentin-Millet, Villeurbanne, all of France

[73] Assignee: Pasteur Merieux Serums & Vaccins, Lyons, France

[21] Appl. No.: 08/860,397

[22] PCT Filed: Oct. 9, 1995

[86] PCT No.: PCT/FR95/01317

§ 371 Date: Dec. 5, 1997

§ 102(e) Date: Dec. 5, 1997

[87] PCT Pub. No.: WO97/13784

PCT Pub. Date: Apr. 17, 1997

[51] Int. Cl.[7] .................................................. A61K 39/02
[52] U.S. Cl. .......................... 424/234.1; 435/7.32; 435/6; 435/252.1
[58] Field of Search ................... 424/234.1, 92; 435/6, 7.32, 252.1

[56] References Cited

U.S. PATENT DOCUMENTS

| | | | |
|---|---|---|---|
| 4,882,271 | 11/1989 | Evans et al. | 435/7 |
| 5,262,156 | 11/1993 | Alemohammad | 424/92 |
| 5,420,014 | 5/1995 | Cripps et al. | 435/7.32 |
| 5,527,678 | 6/1996 | Blaser | 435/6 |
| 5,538,729 | 7/1996 | Czinn et al. | |
| 5,567,594 | 10/1996 | Calenoff | 435/7.32 |
| 5,610,060 | 3/1997 | Ward et al. | 435/252.1 |

FOREIGN PATENT DOCUMENTS

| | | |
|---|---|---|
| 0586266 A1 | 3/1994 | European Pat. Off. . |
| 9411323 | 4/1995 | France . |
| 9003575 | 4/1990 | WIPO . |
| WO 92/03467 | 3/1992 | WIPO . |
| 97 13784 | 4/1997 | WIPO . |

OTHER PUBLICATIONS

Illingworth, D.S., et al., Int. Journal of Medical Microbiology, Virology, Parasitology, and Infectious Diseases, vol. 280/1–2, Sep. 1993, pp. 113–119.

Amini, H. et al, FEMS Immunol. & Med. Microbiol., vol. 16, p 247–255, 1996.

Gray–Owen, S. et al, Gut (Suppl. 2) p8 A62, Abstract No. #3B:47, 1996.

Ho, B et al, Eur. J. Gastroenterol & Hepatol. vol. 7, p 121–124, 1995.

Faulde, M. et al, Electrophoresis, vol. 14, p 945–951, 1993.

Nilius, M. et al, Zbl. Bakt., vol. 280, p 259–272, 1993.

Lelwala–Guruge. J. et al, APMIS, vol. 101, Sep. 1993, p 695–702.

von Wulffen, H. et al, Eur. J. Clin. Microbiol. Infect. Dis., Aug. 1988, p 559–565, vol. 7(4).

Stacey, AR et al, 1990, Eur. J. Clin. Microbiol. Infect. Dis., vol. 9(10), p 732–737.

Nakata, H. et al, J. Gastroenterol, Jun. 1995, vol. 30 (3), p 295–300.

Moran, AP, Feb. 1995, FEMS Immunol. Med Microbiol. vol. 10(3–4) p 271–80.

Fauchere, JL et al, Microbiol Pathogenesis, 1990, vol. 9, p 427–439.

Wadstrom, T, ACTA Microbiol Hung. vol. 38, No. (3–4), 1991, p 164–165.

Emödy, L et al, Scand. J. Infect. Dis., vol. 20, p 353–354, 1988.

Husson, Mo et al, Infect. Immunity, vol. 61(6) Jun. 1993, p2694–2697.

Illingworth, DS., p. S134, # H3–15, Society for Microbiol Ecology and Disease (SOMED), vol. 4(5) (Specissue) 1991, Abstract.

Boren, T. et al, 1993, Science, vol. 262, p. 1892–1895.

Illingworth, D.S. et al., Zbl. Bakt., vol. 280, 1993, p 113–119.

Primary Examiner—James C. Housel
Assistant Examiner—Ginny Allen Portner
Attorney, Agent, or Firm—Clark & Elbing LLP

[57] ABSTRACT

The prevention and treatment of gastric infections caused by the bacterium Helicobacter are disclosed. A newly identified cell-surface protein purified from Helicobacter, and the use thereof as a vaccine, are also disclosed. Said protein is able to bind to human lactoferrin.

3 Claims, 1 Drawing Sheet

HELICOBACTER LACTOFERRIN RECEPTOR

This Application is National Stage Application filed under 35 USC 371 of PCT/FR95/01317 Oct. 9, 1995.

The present invention relates to the prevention and treatment of gastric infections caused by Helicobacter bacteria. The subject of the invention is a newly identified surface protein purified from Helicobacter and its use as a vaccine. This protein is able to bind to lactoferrin of human origin.

Helicobacter pylori is a gram-negative bacterium found at the surface of the gastric mucosa in man. This bacterium is associated with a certain number of gastroduodenal pathologies, for at least some of which it is thought to be the causative pathogen. These pathologies are, in particular, acute or chronic gastritis (inflammation of the mucosa), ulcers (destruction of the mucosa), dyspepsia and certain cancers such as gastric adenocarcinoma.

In this respect, it is already seen to be highly desirable to develop a vaccine for preventing and controlling Helicobacter infections.

Various antigens have already been proposed as potential vaccinating agents: these are, in particular, urease (WO 90/4030), cytotoxin and heat shock protein (WO 93/18150) and adhesins.

However, it is envisaged that, in order to reach maximum efficacy, an anti-Helicobacter vaccine will have to contain more than one antigen. It is therefore necessary to pursue the identification of Helicobacter proteins capable of being employed for this purpose.

The presence of a protein which is capable of binding to human lactoferrin has now been demonstrated in a membrane extract of Helicobacter. Surprisingly, this protein consists of two subunits and may be recognized by monoclonal antibodies which are initially raised against the transferring receptor of Neisseria meningitidis.

Accordingly, the subject of the invention is:

(i) a Helicobacter protein in substantially purified form, the said protein having an apparent molecular weight of about 98 kD or of about 70 kD, as defined after migration on SDS-PAGE gel containing about 10% polyacrylamide, and being capable of being substantially purified from a membrane extract of Helicobacter by affinity chromatography on a lactoferrin column; as well as (ii) a pharmaceutical composition intended for the treatment or prevention of a Helicobacter infection, this composition comprising, as vaccinating principle, at least one protein according to the invention.

The expression "substantially purified protein of 98 or 70 kD" is understood to mean a preparation of this protein which is free of most of the cell constituents of Helicobacter. Obviously, minor contaminants are not excluded.

A protein according to the invention may be obtained from Helicobacter or may be obtained by a recombinant route by expression of the corresponding DNA fragment, in a heterologous system, bacteria, yeasts or mammalian cells.

A protein according to the invention may advantageously be obtained from H. pylori.

A composition according to the invention may be manufactured conventionally. In particular, a protein according to the invention is combined with a pharmaceutically acceptable adjuvant, diluent or support. A composition according to the invention may be administered via any conventional route used in the field of vaccines, in particular via the oral or parenteral route. The administration may take place as a single dosage intake or a dosage intake repeated one or more times after a certain time interval. The appropriate dosage varies as a function of various parameters, for example according to the individual treated or the mode of administration.

EXAMPLE 1

Figure 1A:
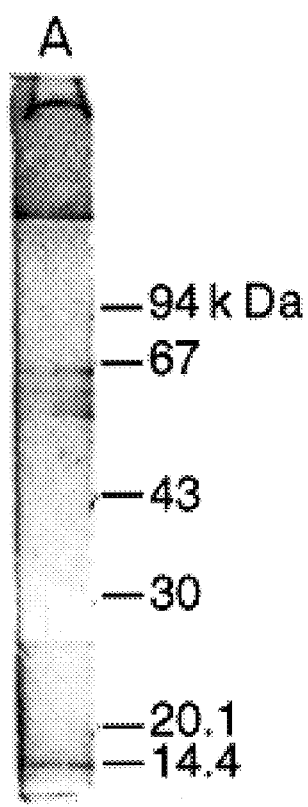
FIGS. 1A—B: The invention is illustrated below with reference to FIG. 1, which shows the electrophoretic profile on SDS-PAGE gel (10% polyacrylamide) of a preparation eluted from a Sepharose 4B-lactoferrin column, after it has been loaded with a membrane extract from H. pylori, as revealed with Coomassie blue FIG. 1A (column A) and with silver nitrate FIG. 1B (column B). The molecular weight standards are phosphorylase B (94 kD), bovine albumin (67 kD), ovalbumin (43 kD), carbonic anhydrase (30 kD), the trypsin inhibitor isolated from soya (soybean trypsin inhibitor) (20.1 kD) and alphalactalbumin (14.4 kD).

Purification of the Lactoferrin Receptor from H. pylori.

1.1 Culturing.

A 25 cm$^2$ flask containing a two-phase medium is inoculated with a strain of H. pylori ATCC No. 43579 (available from ATCC, 12301 Parklawn Drive, Rockville Md—USA) stored in glycerol at −70° C. The two-phase medium comprises a solid phase consisting of 10 ml of Colombia agar (BioMérieux) supplemented with 6% fresh sheep's blood and a liquid phase consisting of 3 ml of Trypticase soya broth (Difco) containing 20% foetal calf serum. The flasks are placed in an airtight bag known as a "generbag" (BBL) and are incubated with gentle rotary stirring at 37° C. for 48 hours under microaerophilic conditions (8–10% $CO_2$, 5–7% $O_2$ and 85–87% $N_2$) obtained by the Microaer System (BBL).

After culturing for 48 hours, a subculture is prepared by inoculating, using this liquid culture, Petri dishes containing a solid agar medium (Colombia agar supplemented with 6% fresh sheep's blood). About 50 Petri dishes are inoculated with a culture obtained in a 25 cm$^2$ flask. These dishes are placed in anaerobic jars under microaerophilic conditions obtained by the Anaerocult C system (Merck). The Petri dishes are then incubated for 4 days at 37° C.

The bacterial lawns are harvested by scraping in the presence of a small volume of PBS (BioMérieux) and by centrifugation. The microorganisms are then washed with PBS in order to remove the residues of the culture medium.

1.2 Purification.

The washed bacterial pellet is suspended in distilled water and subjected to vigorous shaking. This suspension is centrifuged at 18,000×g for 30 min. A certain volume of 25% (w/v) N-lauroylsarcosine is added to the supernatant collected such that the final concentration of Sarkosyl is 0.1% (w/v).

The fraction is placed in a dialysis bag (Spectrum, cutoff threshold of 10,000 daltons) and dialysed against 10 volumes of 50 mM Tris-HCl buffer pH 8.0 containing 0.15 M NaCl, 10 mM EDTA, 0.1% Sarkosyl.

In parallel, a column of Sepharose 4B (Pharmacia) is prepared, on which human lactoferrin (Sigma) has been immobilized. The lactoferrin is grafted onto the Sepharose 4B CNBr resin according to the manufacturer's recommendations. The ligand density is about 5 mg of lactoferrin per ml of gel. The mixture is incubated overnight at +4° C. with rotary stirring. The gel is packed in a 10 ml column; after settling, the gel is washed with about 20 column-volumes of buffer A (50 mM Tris-HCl pH 8.0 containing 10 mM EDTA, 0.1% Sarkosyl, 100 µM PMSF (phenylmethylsulphonyl fluoride, Sigma)) containing 0.15 M NaCl, and then with about 6 column-volumes of buffer A containing 0.5 M NaCl, and lastly with about 6 column-volumes of buffer A containing 1 M NaCl.

The elution is carried out by applying to the column the 50 mM Tris-HCl buffer pH 8.0 containing 10 mM EDTA, 0.05% Sarkosyl, 100 µM PMSF and a guanidine-HCl gradient of from 0 to 2M.

The fractions eluted in the guanidine range from 0.75 to 2M are pooled. This preparation is dialysed against the 50 mM Tris-HCl buffer pH 8.0 and concentrated by rotary evaporation under vacuum.

1.3 Analysis of the purified fraction.

The preparation obtained after affinity chromatography on a column of Sepharose 4B-human lactoferrin is analysed by SDS-PAGE electrophoresis on gel containing 10% acrylamide, according to the Laemmli technique, Nature (1970), 227:680.

After migration, the gel was stained with Coomassie blue. This staining comprises several steps: (1) fixing step: incubation of the gel in a solution of methanol (50 ml), acetic acid (25 ml), trichloroacetic acid (25 ml) and distilled water (900 ml); (2) staining step: incubation of the gel in a mixture of methanol/acetic acid/water (30/10/60) containing 0.25% (w/v) Coomassie blue R250; (3) destaining step in the methanol/acetic acid/water mixture (30/10/60).

Figure 1B:
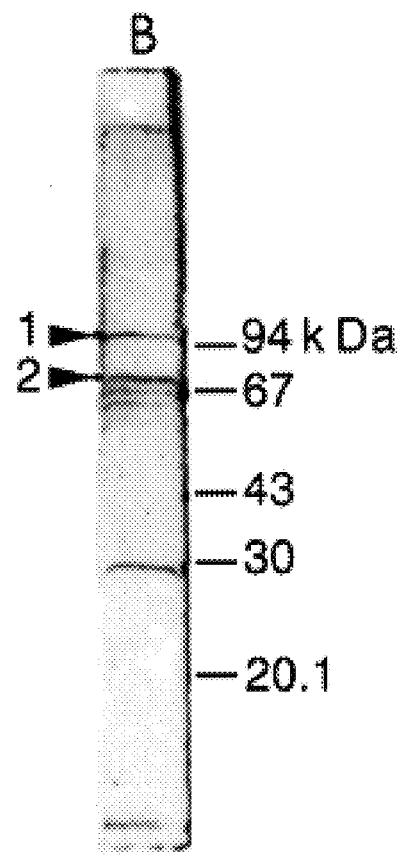

As shown in FIG. 1, column A, this staining reveals a number of bands, none of which are revealed in the 100 kD region.

The preparation obtained was analysed by the silver nitrate staining method.

This staining is carried out on the proteins which are transferred beforehand onto nitrocellulose (Schleicher and Schuell BA 0.45), according to the method described by Kovarik et al., J. Folia Biologica (Praha) 1987, 33:253.

As shown in FIG. 1, column B, the revelation with silver nitrate showed two additional bands not revealed by the staining with Coomassie blue. However, among these bands, it was not possible to say whether one of them corresponded to the lactoferrin receptor.

To overcome this deficiency, the chance idea was had of subjecting a preparation as obtained above to a revelation by immunoaffinity using monoclonal antibodies initially raised against the transferring receptor of N. meningitidis. To do this, a preparation was subjected to SDS-PAGE gel electrophoresis and then transferred onto nitrocellulose.

An SDS-PAGE gel is prepared as above and, after electrophoresis, is transferred onto nitrocellulose. The nitrocellulose is saturated in a blocking buffer (1% (w/v) skimmed milk, 0.9% (w/v) NaCl in 50 mM Tris-HCl pH 8) and then incubated in a solution of anti-(transferring receptor of N. meningitidis) antibody (25 µg IgG/ml in the blocking buffer) for 1 hour at 37° C. with stirring, then washed 3 times with blocking buffer and lastly incubated with a second antibody (anti to the first species) conjugated with peroxidase. The nitrocellulose is finally revealed with a peroxidase-precipitating substrate: 4-chloro-1-naphthol in the presence of $H_2O_2$.

Surprisingly, two bands were thus revealed: one having an apparent molecular weight of 98,000 daltons, the other of 70,000 daltons. The monoclonal antibody study shows that these two bands correspond to two subunits of the same receptor, whereas it is known that the lactoferrin receptor of N. meningitidis is a single-chain receptor (Schryvers & Morris, Infect. Immun. (1988) 56:1144).

EXAMPLE 2

Pharmaceutical Composition for Oral Administration.

The 98 or 70 kD protein which may be obtained as in Example 1 may be encapsulated alone or in the presence of other proteins from H. pylori in gelatin capsules in order to protect the antigen against degradation by the gastric juices, or alternatively may be administered in the presence of sodium bicarbonate. Such formulations have already been used for pharmaceutical compositions (Black et al., Dev. Biol. Stand. (1983) 53). The protein may also be encapsulated in PLGA (copolymers of glycolic acid and of lactic acid) microspheres according to the procedure described elsewhere (Eldridge et al., Curr. Top. Microbiol. Immunol. (1989) 146:59). The protein may also be included in liposomes prepared according to the widely described conventional methods (Liposomes: a Practical Approach, eds. RRC New, D. Rickwood & B.D. Hames, 1990, Oxford University Press, ISBN 0-19-963077-1).

Independently of the formulation, the amount of protein administered orally to man is from about 1 to 10 mg per dosage intake, and at least 3 dosage intakes at 4-weekly intervals are recommended.

EXAMPLE 3

Pharmaceutical Composition for Parenteral Administration.

The 98 or 70 kD protein which may be obtained as in Example 1 is adsorbed onto alumina gel in an entirely conventional manner. The protein dissolved at a concentration of 1 mg/ml in a buffer whose pH is close to 6.5 is placed in contact for 1 hour with aluminium hydroxide with a measured $Al^{+++}$ content of 10 mg/ml. The final composition of the preparation is as follows: a protein according to the invention, 50 µg/ml, 250 µg/ml $Al^{+++}$, 1/1000 Merthiolate, the whole in PBS.

As in the case of the oral administration, 3 injections are recommended, each spaced 4 weeks apart from the previous one.

We claim:

1. A Helicobacter protein in substantially purified form, said protein:

having affinity for human lactoferrin, and consisting of two associated sub-units having apparent molecular weights of about 98 kDa and about 70 kDa, respectively, as defined after migration of the subunits on an SDS-PAGE gel containing 10% polyacrylamide.

2. A protein according to claim 1, wherein said protein is an *H. pylori* protein.

3. A method of stimulating an immune response to *Helicobacter pylori* in a subject comprising administering the substantially purified protein of claim 1 to a subject.

* * * * *

UNITED STATES PATENT AND TRADEMARK OFFICE
CERTIFICATE OF CORRECTION

PATENT NO. : 6,086,893            Page 1 of 1
DATED : July 11, 2000
INVENTOR(S) : Monique Dupuy, Ling Lissolo, Marie-José Bernadette Quentin-Millet It is certified that error appears in the above-identified patent and that said Letters Patent is hereby corrected as shown below:

<u>Column 3,</u>
Line 47, replace "transferring" with -- transferrin --;
Line 54, replace "transferring" with -- transferrin --.

Signed and Sealed this

Thirteenth Day of November, 2001

Attest:

*Nicholas P. Godici*

NICHOLAS P. GODICI
*Attesting Officer*      *Acting Director of the United States Patent and Trademark Office*